United States Patent [19]

Banwer

[11] Patent Number: 5,342,829
[45] Date of Patent: Aug. 30, 1994

[54] DIISOPROPYL ADIPATE AS A SOLVENT FOR FRAGRANCE EXTRACTS

[75] Inventor: Mark Banwer, Great Neck, N.Y.

[73] Assignee: Alan Kesten, East Hills, N.Y.

[21] Appl. No.: 31,588

[22] Filed: Mar. 16, 1993

[51] Int. Cl.$^5$ ................................................ A61K 7/46
[52] U.S. Cl. ............................................ 512/2; 512/3
[58] Field of Search ........................ 512/2, 3; 560/190

[56] References Cited

U.S. PATENT DOCUMENTS

| 2,422,145 | 6/1947 | Taylor | 512/3 |
| 3,759,806 | 9/1973 | Doctor | 204/158 R |
| 3,945,950 | 3/1976 | Vosganiantz | 512/2 |
| 4,110,626 | 8/1978 | Katada et al. | 512/2 |
| 5,081,104 | 1/1992 | Orson | 512/3 |

OTHER PUBLICATIONS

Higashi et al, Chem. Abst; vol. 105, #213,937; (1986).

Primary Examiner—James H. Reamer
Attorney, Agent, or Firm—Frederick H. Rabin

[57] ABSTRACT

Fragrance extract compositions, such as perfumes, toilet water, splashes and aftershaves, in which the solvent consists of a $C_1$ to $C_4$ ester of adipic acid. The preferred ester is diisopropyl adipate.

6 Claims, No Drawings

DIISOPROPYL ADIPATE AS A SOLVENT FOR FRAGRANCE EXTRACTS

FIELD OF THE INVENTION

This relates to fragrance extracts, such as perfume, toilet water, eau de cologne and aftershaves, in which the solvent consists essentially of a diester of adipic acid. More particularly, the invention relates to fragrance extracts in which the usual ethanol solvent is replaced in its entirety by diisopropyl adipate.

BACKGROUND OF THE INVENTION

A fragrance extract is a solution of a perfume oil in an appropriate solvent or vehicle, which is usually ethyl alcohol. Occasionally, depending on the end use of the product, cost considerations and solubility characteristics of the perfume oil, a small amount of water may be added to the alcohol. In addition to serving as a solvent for perfume oils, the alcohol also contributes to the so-called "lift" of the "notes"—i.e. the various scent fractions—of the perfume oil. Ethyl alcohol is a volatile compound and, in view of new governmental regulations restricting the use of volatile organic compounds (VOCs), it would be desirable to develop an alternative solvent for fragrance extracts which would not be classified as a VOC but which would still provide the recognized advantages of ethyl alcohol. Such solvent would not substantially contribute to or adversely affect the odor of the fragrance extract, would be safe both environmentally and for human use, and would provide the fragrance extract with physical and performance characteristics similar to those provided by ethyl alcohol.

Accordingly, it is the primary object of this invention to provide a solvent for fragrance extract compositions which would be a replacement for ethyl alcohol in which, at the same time, would not adversely alter the characteristics of the fragrance extract composition.

SUMMARY OF THE INVENTION

This invention provides a fragrance composition which consists essentially of a perfume oil in concentrations ranging from about 0.5 to about 60 percent in a solvent consisting of an adipic acid diester in which the ester group has from 1 to 4 carbon atoms. The preferred solvents are dimethyl adipate, diisopropyl adipate and dibutyl adipate, with diisopropyl adipate being most preferred.

DETAILED DISCLOSURE

The term "fragrance extract composition" as used herein is intended to encompass all fragrance compositions comprising perfume oil and a solvent. Thus, "fragrance extract" encompasses perfumes, toilet waters, colognes, aftershaves, after bath splashes, etc., all of which products have varying percentages of perfume oils. There are no clear specifications as to what particular concentration of perfume oil is required in perfume, toilet water, etc., and many of these terms are used interchangeably and overlap. In general, however, the perfume oil content of these products is in the following ranges:

| | |
|---|---|
| Perfume | 10–60% |
| Toilet Water or Cologne | 2–15% |
| Splashes | 1–4% |
| Aftershaves | 0.5–6% | the foregoing percentages being by weight.

The perfume oil itself does not ordinarily consist of a single natural or synthetic material, but is most often a combination of many materials which are carefully blended by perfumers to achieve the desired characteristics of odor, consistency, lasting power, etc.

The adipic acid esters usable as solvents are the $C_1$–$C_4$ diesters of adipic acid including dimethyl adipate, diethyl adipate, diisopropyl adipate and dibutyl adipate. The most preferred ester is diisopropyl adipate.

Diisopropyl adipate is a clear liquid, insoluble in water, with a boiling point of 264° C. and a melting point of −4° C.; it has a specific gravity in the range of 0.950 to 0.962. the compound has been used in various cosmetics applications, such as an emollient in shaving lotions and hair tonics. Thus, it has been used with perfume oils in ethanol and aqueous ethanol solvent systems, but diisopropyl adipate has never been regarded as a solvent. The use of diisopropyl adipate as a sole solvent in a fragrance extract composition has not heretofore been known.

The compositions of this invention consist essentially of a perfume oil and a $C_1$–$C_4$ diester of adipic acid. The amount of perfume oil present in the composition will depend upon the nature of the fragrance extract composition. Thus, for perfume, the fragrance comprises from about 10 to about 60 weight percent and the ester comprises from 40 to 90 percent of the composition; preferably, the fragrance comprises from 10 to 35 weight percent and the ester comprises from 65 to 90 weight percent of the composition. For toilet water or cologne, the perfume oil comprises from about 2 to about 15 percent, and the ester comprises from 85 to 98 percent of the composition. For after bath splashes, the perfume oil comprises from about 1 to about 4 percent of the composition. And, for aftershaves, the perfume oil comprises from about 0.5 to about 6 percent of the fragrance extract composition, and the ester comprises from 94 to 99.5 percent of said composition.

Diisopropyl adipate is one of the many emollients or humectants known for use in cosmetic preparations, but is not known for use in fragrance extracts within the meaning of this invention. A series of experiments was run in order to determine whether other known humectants and emollients would also be capable of serving as the sole solvent in fragrance extract compositions. The experiments included dimethyl adipate and dibutyl adipate, whose use is also within the scope of this invention. Fragrance extract compositions with one of ten known cosmetic ingredients were evaluated and compared for spray pattern and skin feel against similar fragrance extract compositions in which the solvent was ethyl alcohol. The compounds tested were diisodecyl adipate, diisopropyl sebacate, diisopropyl adipate, isopropyl myristate, isopropyl palmitate, diisopropyl dilinoleate, dioctyl adipate, dipropylene glycol, dimethyl adipate and dibutyl adipate. The ethyl alcohol was denatured by the addition of one percent diethyl phthalate.

Tests were run at concentrations of 1 percent and 35 percent perfume oil using both pump spray and an aerosol spray container containing 20 percent weight of Propellent A-46, which consists of 84 percent isobutane and 16 percent n-propane.

The spray pattern was evaluated on a scale of 1 to 5, the spray pattern attained by the alcohol formulation being regarded as 1. Skin feel evaluation was also on a scale of 1 to 5 as follows:

1—Non-oily;
2—Slightly oily;
3—Moderately oily;
4—Semi-oily;
5—Very oily.

EXAMPLE 1
1% Perfume Oil - Pump Spray

| Solvent | Spray Pattern | Skin Feel |
| --- | --- | --- |
| ethanol | 1 | 1 |
| diisodecyl adipate | 4 | 5 |
| diisopropyl sebacate | 1 | 3 |
| diisopropyl adipate | 1 | 2 |
| isopropyl myristate | 1 | 5 |
| isopropyl palmitate | 1 | 4 |
| diisopropyl dilinoleate | 5 | 5 |
| dioctyl adipate | 5 | 5 |
| dipropylene glycol | 5 | 5 |
| dimethyl adipate | 1 | 4 |
| dibutyl adipate | 1 | 3 |

EXAMPLE 2
1% Perfume Oil - Aerosol Spray

| Solvent | Spray Pattern | Skin Feel |
| --- | --- | --- |
| ethanol | 1 | 1 |
| diisodecyl adipate | 1 | 5 |
| diisopropyl sebacate | 1 | 3 |
| diisopropyl adipate | 1 | 2 |
| isopropyl myristate | 1 | 5 |
| isopropyl palmitate | 1 | 4 |
| diisopropyl dilinoleate | 1 | 5 |
| dioctyl adipate | 1 | 5 |
| dipropylene glycol | 1 | 5 |
| dimethyl adipate | 1 | 4 |
| dibutyl adipate | 1 | 3 |

EXAMPLE 3
35% Perfume Oil - Pump Spray

| Solvent | Spray Pattern | Skin Feel |
| --- | --- | --- |
| ethanol | 1 | 1 |
| diisodecyl adipate | 1 | 5 |
| diisopropyl sebacate | 1 | 3 |
| diisopropyl adipate | 1 | 2 |
| isopropyl myristate | 1 | 5 |
| isopropyl palmitate | 1 | 4 |
| diisopropyl dilinoleate | 5 | 5 |
| dioctyl adipate | 5 | 5 |
| dipropylene glycol | 5 | 5 |
| dimethyl adipate | 1 | 2 |
| dibutyl adipate | 1 | 3 |

EXAMPLE 4
35% Perfume Oil - Aerosol Spray

| Solvent | Spray Pattern | Skin Feel |
| --- | --- | --- |
| ethanol | 1 | 1 |
| diisodecyl adipate | 1 | 5 |
| diisopropyl sebacate | 1 | 3 |
| diisopropyl adipate | 1 | 2 |
| isopropyl myristate | 1 | 5 |
| isopropyl palmitate | 1 | 4 |
| diisopropyl dilinoleate | 1 | 5 |
| dioctyl adipate | 1 | 5 |
| dipropylene glycol | 1 | 5 |
| dimethyl adipate | 1 | 2 |
| dibutyl adipate | 1 | 3 |

While there have been described what are at present considered to be the preferred embodiments of this invention, it will be obvious to those skilled in the art that various changes and modifications may be made therein without departing from the invention, and it is therefore aimed to cover all such changes and modifications as fall within the true spirit and scope of the invention.

I claim:

1. A fragrance composition consisting essentially of a perfume oil and diisopropyl adipate.

2. A composition according to claim 1 in which the perfume oil is present in an amount of from about 10 to about 60 weight percent.

3. A composition according to claim 2 in which the perfume oil is present in an amount of from about 10 to about 35 weight percent.

4. A composition according to claim 1 in which the perfume oil is present in an amount from 2 to about 15 weight percent.

5. A composition according to claim 1 in which the perfume oil is present in an amount of from about 1 to about 4 weight percent.

6. A composition according to claim 1 in which the perfume oil is present in an amount of rom about 0.5 to about 6 weight percent.

* * * * *